(12) United States Patent
Lenke et al.

(10) Patent No.: US 8,951,257 B2
(45) Date of Patent: Feb. 10, 2015

(54) SPINAL CORRECTION SYSTEM AND METHOD

(75) Inventors: Lawrence G. Lenke, St. Louis, MO (US); Jason May, Cordova, TN (US); William Alan Rezach, Atoka, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 136 days.

(21) Appl. No.: 13/397,365

(22) Filed: Feb. 15, 2012

(65) Prior Publication Data

US 2013/0211453 A1 Aug. 15, 2013

(51) Int. Cl.
*A61B 17/70* (2006.01)

(52) U.S. Cl.
USPC ............................................. 606/86 A

(58) Field of Classification Search
USPC ......... 606/86 A, 279, 281, 54–246, 248–252, 606/258, 86 B
See application file for complete search history.

(56) References Cited

U.S. PATENT DOCUMENTS

| | | | | |
|---|---|---|---|---|
| 4,505,268 A | * | 3/1985 | Sgandurra | 606/53 |
| 4,907,577 A | * | 3/1990 | Wu | 606/87 |
| 4,957,495 A | * | 9/1990 | Kluger | 606/58 |
| 5,478,340 A | * | 12/1995 | Kluger | 606/86 A |
| 5,797,910 A | * | 8/1998 | Martin | 606/57 |
| 6,090,113 A | * | 7/2000 | Le Couedic et al. | 606/914 |
| 6,123,707 A | * | 9/2000 | Wagner | 606/86 A |
| 6,214,004 B1 | * | 4/2001 | Coker | 606/86 A |
| 6,238,396 B1 | | 5/2001 | Lombardo | |
| 6,332,780 B1 | * | 12/2001 | Traxel et al. | 434/267 |
| 6,332,887 B1 | * | 12/2001 | Knox | 606/87 |
| 6,530,929 B1 | * | 3/2003 | Justis et al. | 606/103 |
| 6,585,738 B1 | * | 7/2003 | Mangione et al. | 606/258 |
| 6,605,088 B1 | * | 8/2003 | St. Onge et al. | 606/54 |
| 6,749,613 B1 | * | 6/2004 | Conchy et al. | 606/57 |
| 6,755,828 B2 | * | 6/2004 | Shevtsov et al. | 606/54 |
| 7,918,792 B2 | * | 4/2011 | Drzyzga et al. | 600/215 |
| 8,007,516 B2 | * | 8/2011 | Chao et al. | 606/246 |
| 8,097,021 B1 | * | 1/2012 | Kornel | 606/248 |
| 8,277,453 B2 | * | 10/2012 | Kave et al. | 606/86 A |
| 8,357,184 B2 | * | 1/2013 | Woolley et al. | 606/279 |
| 8,608,782 B1 | * | 12/2013 | Rovner | 606/264 |
| 2002/0049444 A1 | * | 4/2002 | Knox | 606/61 |
| 2005/0033291 A1 | * | 2/2005 | Ebara | 606/53 |
| 2005/0090822 A1 | * | 4/2005 | DiPoto | 606/61 |
| 2005/0171540 A1 | * | 8/2005 | Lim et al. | 606/61 |
| 2005/0234449 A1 | * | 10/2005 | Aferzon | 606/61 |
| 2005/0234452 A1 | * | 10/2005 | Malandain | 606/61 |
| 2006/0167454 A1 | * | 7/2006 | Ludwig et al. | 606/61 |

(Continued)

FOREIGN PATENT DOCUMENTS

KR 101030065 B1 4/2011

*Primary Examiner* — Mary Hoffman

(57) ABSTRACT

A spinal correction system comprises an elongate member extending between a first end including a first inner surface defining a first cavity and a second end including a collar having a second inner surface defining a second cavity. The second cavity is movable relative to the elongate member in at least one orientation. The second end defining an elongated cavity. A first extender defines a first outer surface and a second extender defines a second outer surface. The elongate member is disposable between a first configuration and a second configuration such that the second cavity is movable in the at least one orientation to a position such that the first inner surface is forcibly disposable in a fixed engagement with the first outer surface and the interior surface is forcibly disposed in a fixed engagement with at least a portion of the collar. Methods of use are disclosed.

17 Claims, 10 Drawing Sheets

(56) References Cited

U.S. PATENT DOCUMENTS

| | | | |
|---|---|---|---|
| 2006/0200135 A1* | 9/2006 | Sherman et al. | 606/61 |
| 2007/0049931 A1* | 3/2007 | Justis et al. | 606/61 |
| 2007/0112351 A1* | 5/2007 | Assell et al. | 606/61 |
| 2007/0162002 A1* | 7/2007 | Tornier | 606/61 |
| 2007/0162009 A1* | 7/2007 | Chao et al. | 606/61 |
| 2007/0162010 A1* | 7/2007 | Chao et al. | 606/61 |
| 2007/0173831 A1* | 7/2007 | Abdou | 606/61 |
| 2007/0213716 A1* | 9/2007 | Lenke et al. | 606/61 |
| 2007/0233079 A1* | 10/2007 | Fallin et al. | 606/61 |
| 2007/0299444 A1* | 12/2007 | DiPoto et al. | 606/61 |
| 2008/0039841 A1* | 2/2008 | Casutt et al. | 606/61 |
| 2008/0077138 A1* | 3/2008 | Cohen et al. | 606/61 |
| 2008/0086134 A1 | 4/2008 | Butler et al. | |
| 2008/0172062 A1* | 7/2008 | Donahue et al. | 606/104 |
| 2009/0018593 A1* | 1/2009 | Barrus et al. | 606/86 A |
| 2009/0062858 A1* | 3/2009 | Dziedzic et al. | 606/278 |
| 2009/0171391 A1* | 7/2009 | Hutton et al. | 606/246 |
| 2009/0216278 A1* | 8/2009 | Song | 606/264 |
| 2010/0004695 A1* | 1/2010 | Stad et al. | 606/86 A |
| 2010/0030283 A1* | 2/2010 | King et al. | 606/86 A |
| 2010/0057127 A1 | 3/2010 | McGuire et al. | |
| 2010/0298885 A1* | 11/2010 | Tribus | 606/279 |
| 2010/0324610 A1* | 12/2010 | Bridwell et al. | 606/86 A |
| 2010/0331901 A1* | 12/2010 | Iott et al. | 606/86 A |
| 2011/0106082 A1* | 5/2011 | Kave et al. | 606/70 |
| 2011/0137358 A1* | 6/2011 | Manninen | 606/86 R |
| 2011/0172714 A1* | 7/2011 | Boachie-Adjei et al. | 606/264 |
| 2011/0196426 A1* | 8/2011 | Peukert et al. | 606/279 |
| 2012/0083853 A1* | 4/2012 | Boachie-Adjei et al. | 606/86 A |
| 2012/0191143 A1* | 7/2012 | Nayet et al. | 606/86 A |
| 2012/0221063 A1* | 8/2012 | Abdou | 606/86 A |
| 2013/0172947 A1* | 7/2013 | Greenberg | 606/86 A |
| 2013/0184763 A1* | 7/2013 | McClintock et al. | 606/279 |
| 2013/0245694 A1* | 9/2013 | Choi et al. | 606/279 |

* cited by examiner

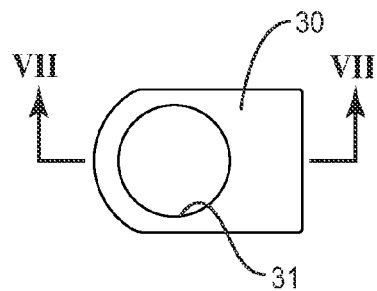 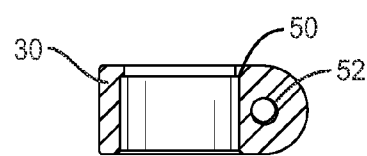
FIG. 6  FIG. 7
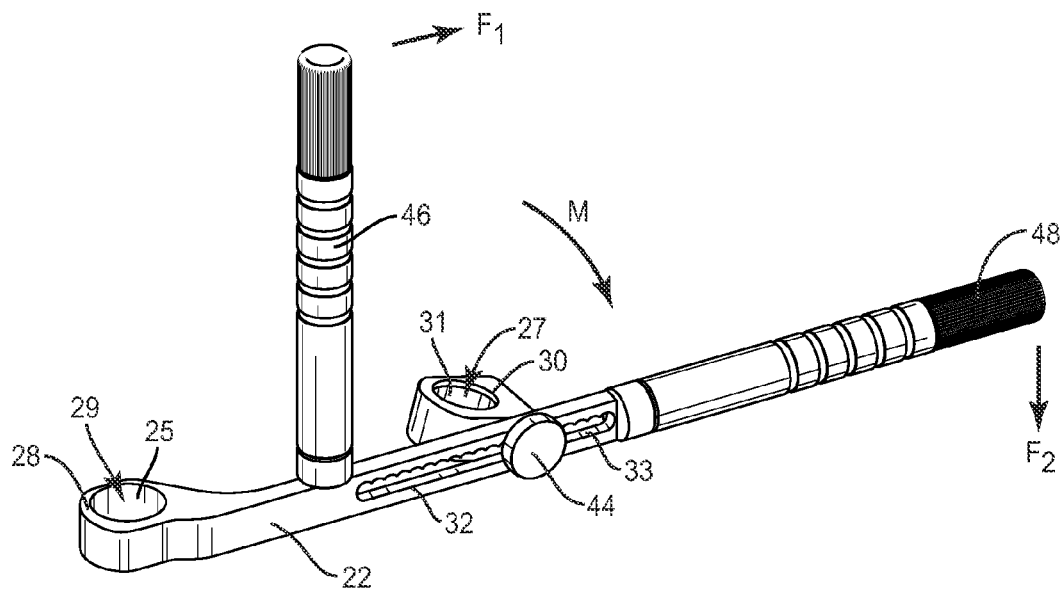
FIG. 8

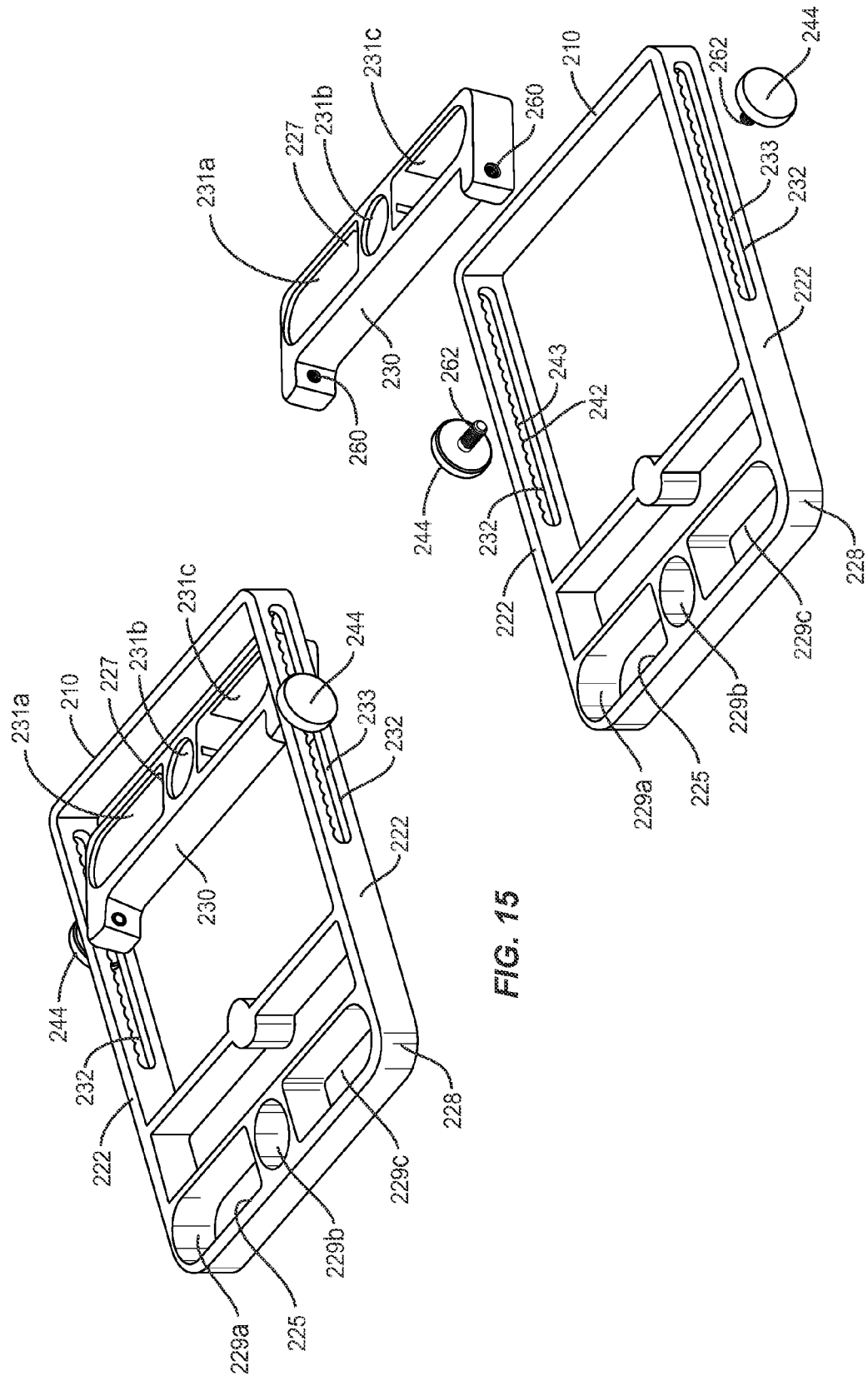

SPINAL CORRECTION SYSTEM AND METHOD

TECHNICAL FIELD

The present disclosure generally relates to medical devices for the treatment of musculoskeletal disorders, and more particularly to a surgical system and method for correction of a spine disorder.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. Correction treatments may employ implants that are manipulated for engagement with vertebrae in the spinal column in an effort to position and align one or more vertebrae. This disclosure describes an improvement over these prior art technologies.

SUMMARY

Accordingly, a surgical system and method for correction of a spine disorder is provided. In one particular embodiment, in accordance with the principles of the present disclosure, a spinal correction system comprises at least one elongate member defining a longitudinal axis and extending between a first end and a second end. The first end includes a first inner surface defining a first cavity and the second end includes a collar having a second inner surface defining a second cavity. The second cavity is movable relative to the elongate member in at least one orientation. The second end includes an interior surface defining an elongated cavity. At least one first extender defines a first outer surface configured for engagement with the first inner surface. At least one second extender defines a second outer surface configured for engagement with the second inner surface. The at least one elongate member is disposable between a first configuration and a second configuration such that the second cavity is movable in the at least one orientation to a position such that the first inner surface is forcibly disposed in a fixed engagement with the first outer surface and the interior surface is forcibly disposed in a fixed engagement with at least a portion of the collar.

In one embodiment, the spinal correction system comprises at least one bridge member defining a first longitudinal axis and extending between a first end and a second end. The first end includes a first collar defining a first opening and the second end includes a second collar defining a second opening that defines a second axis oriented transverse to the first longitudinal axis. The second end further including an interior surface defining an elongated slot configured for moving the second collar relative to the bridge member in an angular orientation and an axial orientation. At least one first extender defines an outer surface configured for engagement with the first collar and disposal with a concave portion of a spine. At least one second extender defines an outer surface configured for engagement with the second collar and disposal with a convex portion of the spine. The at least one bridge member is disposable between a first configuration and a second configuration such that the second collar is movable to a position such that the second axis is selectively angularly oriented relative to the first longitudinal axis and the second collar is selectively axially oriented relative to the slot such that the first inner surface is forcibly disposed in a pivot coupling with the outer surface of the first extender and the interior surface is forcibly disposed in a fixed engagement with at least a portion of the second collar.

In one embodiment, the spinal correction system comprises a plurality of bridge members. Each bridge member defines a longitudinal axis and extending between a first end and a second end. The first end of each bridge member includes a first collar defining a first opening and the second end of each bridge member including a second collar defining a second opening that defines a second axis oriented transverse to the respective longitudinal axis. The second end of each bridge member further includes an interior surface defining an elongated slot configured for moving the second collar relative to the respective elongate member in an angular orientation and an axial orientation. The system further comprises a plurality of concave extenders. Each concave extender defines an outer surface configured for engagement with the first collar of one of the plurality of bridge members. The system further comprises a plurality of convex extenders. Each convex extender defines an outer surface configured for engagement with the second collar of a one of the plurality of bridge members. A link member extends through the slots of each of the bridge members. The plurality of bridge members are collectively disposable between a first configuration and a second configuration such that the second collar of each bridge member is movable to a position such that the second axis is angularly oriented relative to the first longitudinal axis and the second collar is axially oriented relative to the slot such that the first collar is forcibly disposed in a pivot coupling with the outer surface of the first extender and the second collar is forcibly disposed in a fixed engagement with the interior surface so that the plurality of bridge members are configured for derotation of vertebrae such that a first force oriented in a first direction is applied to the first end of each bridge member and a second force oriented in a second direction is applied to the second end of each bridge member.

BRIEF DESCRIPTION OF THE DRAWINGS

The present disclosure will become more readily apparent from the specific description accompanied by the following drawings, in which:

FIG. 6 is a top view of a collar of the system shown in FIG. 1;

FIG. 7 is a side cross section view of the collar shown in FIG. 6 taken along lines VII-VII;

FIG. 8 is a perspective view of components of the system shown in FIG. 1;

FIG. 15 is a perspective view of an elongated member of the system shown in FIG. 14;

FIG. 16 is a perspective view of the elongated member shown in FIG. 15 with parts separated;

Like reference numerals indicate similar parts throughout the figures.

DETAILED DESCRIPTION

Figure 1:
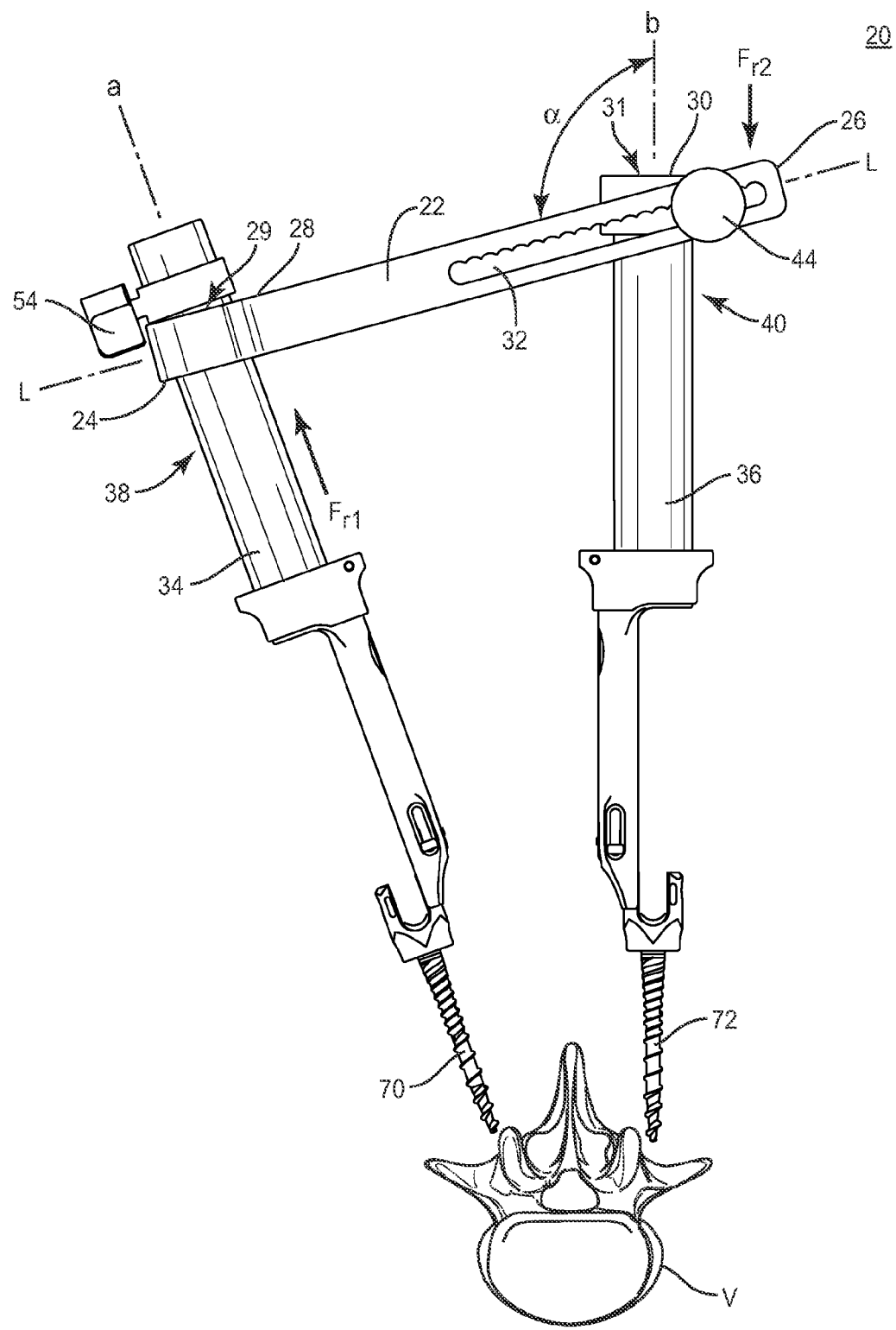
FIG. 1 is a side view of one particular embodiment of a system in accordance with the principles of the present disclosure.

The exemplary embodiments of the spinal correction system and related methods of use disclosed are discussed in terms of medical devices for the treatment of musculoskeletal disorders and more particularly, in terms of a spinal correction system and method that facilitates implant delivery and treatment of a spine. It is envisioned that the spinal correction system can include extenders, reducers and translators, which can be used to introduce a vertebral construct such as a rod to a bone fastener, such as a bone anchor or bone screw. For example, an extender can include bone anchor attachment features on one or both sides of the instrument. It is contemplated that the system may be used with a reducer assembly to introduce a rod into a bone fastener.

In one embodiment, the system includes a segmental derotation apparatus, which comprises an adjustable link for connecting at least two screw extenders in an axial plane. The segmental derotation apparatus includes a link having a bridge bar and a hinge. The bridge bar connects to a screw extender, for example, a concave extender, while the hinge connects to another screw extender, for example, a convex extender. The adjustable link provides for varying distances between extenders by having a scalloped slot that allows movement when external force is not applied. Upon application of external forces, the hinge locks into one of the scallops of the scalloped slots to provide rigidity along the bridge bar. The bridge bar connects to an extender by sliding over a top surface of the extender. The hinge also slides over an extender. The hinge may include a lip, such as, for example, a shoulder that prevents ventral translation of the extender to maintain the hinge from sliding down the extender shaft. By applying a downward force to a handle or hinge side of the bridge bar, a moment is applied about the hinge creating a pivot coupling between the bridge bar of an associated extender. It is contemplated that a setscrew could be used to lock the bridge bar onto an extender. It is further contemplated that a linking member may be employed to link multiple bridge bars together so that all levels operate as one global unit.

In one embodiment, the system includes a global derotation apparatus, which comprises locking onto only one vertebral level in an axial plane. For example, two levels could be linked together. It is envisioned that one or two levels above and below an apex can be locked as a unit so that correction of the unit can be achieved. It is contemplated that the system can be employed with a method that allows for distraction and kyphosis adjustments while the unit is attached with the extenders.

It is envisioned that the spinal correction system may include instruments that are connected or attached to an extender(s) such as, for example, a lateral translation handle or derotation instruments. In one embodiment, one or all of the components of the surgical system are disposable, peel-pack, pre-packed sterile devices used with a spinal correction system. One or all of the components of the spinal correction system may be reusable. The spinal correction system may be configured as a kit with multiple sized and configured components.

It is envisioned that the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. It is contemplated that the present disclosure may be employed with other osteal and bone related applications, including those associated with diagnostics and therapeutics. It is further contemplated that the disclosed surgical system and methods may be alternatively employed in a surgical treatment with a patient in a prone or supine position, and/or employ various surgical approaches to the spine, including anterior, posterior, posterior mid-line, direct lateral, postero-lateral, and/or antero-lateral approaches, and in other body regions. The present disclosure may also be alternatively employed with procedures for treating the lumbar, cervical, thoracic and pelvic regions of a spinal column. The system and methods of the present disclosure may also be used on animals, bone models and other non-living substrates, such as, for example, in training, testing and demonstration.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a spinal correction system and related methods of employing the surgical system in accordance with the principles of the present disclosure. Alternate embodiments are also disclosed. Reference will now be made in detail to the exemplary embodiments of the present disclosure, which are illustrated in the accompanying figures. Turning now to FIGS. 1-12, there is illustrated components of a surgical system, such as, for example, a spinal correction system 20 in accordance with the principles of the present disclosure.

The components of spinal correction system 20 can be fabricated from biologically acceptable materials suitable for medical applications, including metals, synthetic polymers, ceramics and bone material and/or their composites, depending on the particular application and/or preference of a medical practitioner. For example, the components of spinal correction system 20, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKEL-ITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglyclolide, polytyrosine carbonate, polycaroplaetohe and their combinations.

Various components of spinal correction system 20 may have material composites, including the above materials, to achieve various desired characteristics such as strength, rigidity, elasticity, compliance, biomechanical performance, durability and radiolucency or imaging preference. The components of spinal correction system 20, individually or collectively, may also be fabricated from a heterogeneous material such as a combination of two or more of the above-described materials. The components of spinal correction system 20 may be monolithically formed, integrally connected or include fastening elements and/or instruments, as described herein.

Spinal correction system 20 is employed, for example, with an open or mini-open, minimal access and/or minimally invasive including percutaneous surgical technique for engagement with an implant, such as, for example, a bone fastener for a correction treatment at a surgical site within a body of a patient, for example, a section of a spine to treat various spine pathologies, such as, for example, adolescent idiopathic scoliosis and Scheuermann's kyphosis. In one embodiment, the components of spinal correction system 20 are configured to deliver and introduce an implant, such as, for example, a vertebral construct such as a rod to a bone fastener.

Spinal correction system 20 includes an elongate member, such as for example, a bridge member 22 defining a longitudinal axis L. Bridge member 22 extends between a first end 24 and a second end 26. It is contemplated that system 20 may include one or a plurality of elongate members 22.

Figure 2:
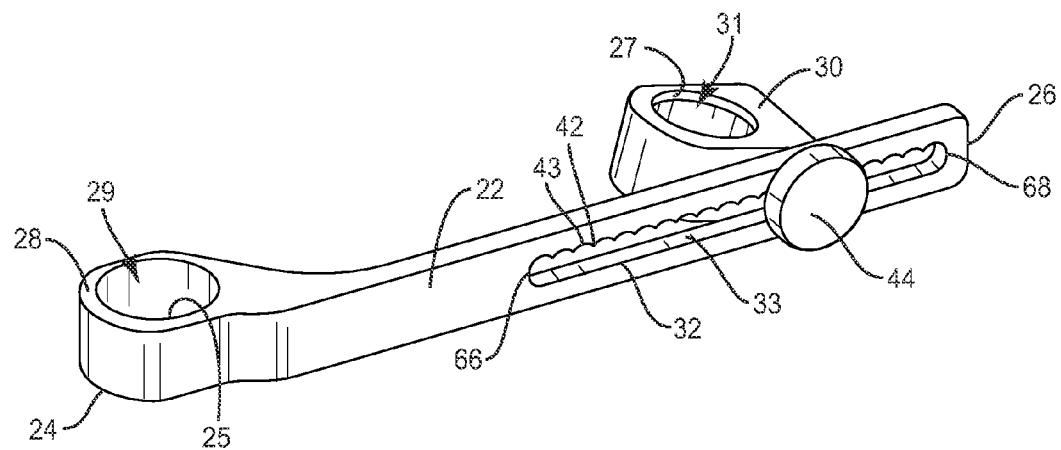
FIG. 2 is a perspective view of components of the system shown in FIG. 1.
Figure 3:
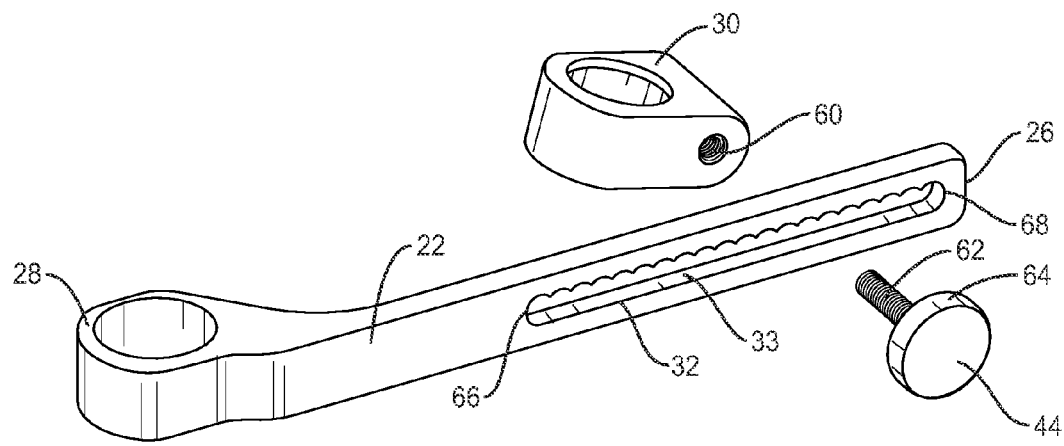
FIG. 3 is a perspective view of components of the system shown in FIG. 1 with parts separated.
Figure 4:
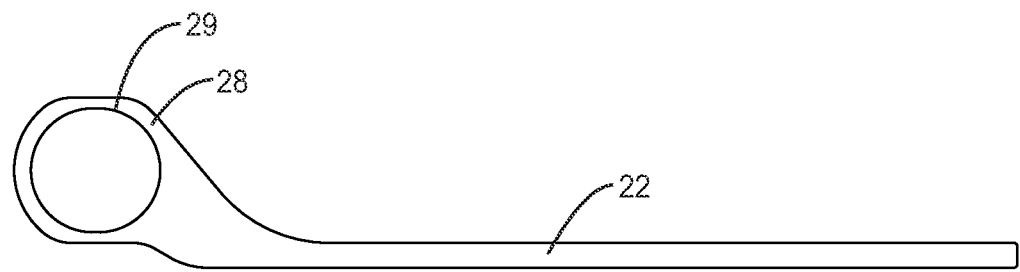
FIG. 4 is atop view of an elongated member of the system shown in FIG. 1.
Figure 5:
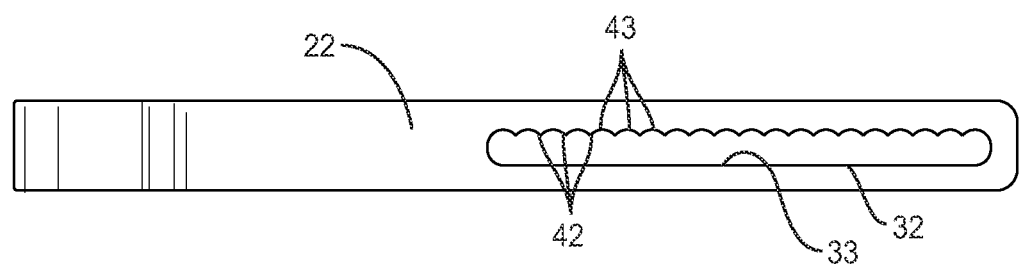
FIG. 5 is a side view of the elongated member shown in FIG. 2.

First end 24 includes a first collar 28 having an inner surface 25, as shown in FIGS. 2 and 3. Inner surface 25 defines a first cavity, such as for example, a first opening 29. It is envisioned that opening 29 may be variously configured and dimensioned, such as, for example, round, oval, oblong, square, rectangular, polygonal, irregular, uniform, non-uniform, offset, staggered, tapered, consistent or variable, depending on the requirements of a particular application. In one embodiment, the first cavity may extend through only a portion of first collar 28 and not completely through. Opening 29 defines a first axis a. First axis a is disposed at a transverse orientation relative to axis L. Opening 29 is configured for disposal of a surgical instrument, such as, for example, an extender 34 described below.

Second end 26 includes a second collar 30 having a second inner surface 27. Inner surface 27 defines a second cavity, such as for example, a second opening 31. It is envisioned that opening 31 may be variously configured and dimensioned, such as, for example, round, oval, oblong, square, rectangular, polygonal, irregular, uniform, non-uniform, offset, staggered, tapered, consistent or variable, depending on the requirements of a particular application. In one embodiment, the second cavity may extend through only a portion of second collar 30 and not completely through. Opening 31 defines a second axis b. Second axis b is disposed at a transverse orientation relative to axis L. Opening 31 is configured for disposal of a surgical instrument, such as, for example, an extender 36 described below.

Collar 30 includes a treaded opening 60 and a hinge 44. Hinge 44 includes a post 62 configured for engagement with opening 60. Hinge 44 includes a knob 64 for manipulation. Post 62 can be a threaded or smooth pin or other connecting device such as a set screw. Hinge 44 is configured for movable disposal relative to second end 26, as described below.

Second collar 30 includes a flange, such as for example, a shoulder 50, as shown in FIGS. 6 and 7, configured for preventing translation of second collar 30 onto extender 36, for example, ventral translation of second collar 30 along second extender 36. Second end 26 includes an interior surface 33 that defines an elongated cavity, such as, for example, a slot 32 configured for movement of second collar 30 including hinge 44 relative to the bridge member 22 in at least one orientation. In one embodiment, the at least one orientation includes an angular rotation of axis b relative to axis L through an angle α and/or an axial translation of second collar 30 along axis L and relative to second end 26. It is contemplated that angle α includes a range of 0 to 360 degrees.

Interior surface 33 of slot 32 includes projections 42 that define recesses 43 configured for disposal of post 62. Inner surface 33 has a scalloped configuration for adjustable and/or selective fixation of second collar 30 along slot 32. It is contemplated that interior surface 33 can have one or a plurality of projections and/or recesses. It is further contemplated that interior surface 33 may have alternate surface configurations to enhance fixation with hinge 44, such as, for example, rough, arcuate, undulating, mesh, porous, semi-porous, dimpled and/or textured according to the requirements of a particular application. Slot 32 extends between a first end 66 and a second end 68. Hinge 44 moves along the length of slot 32 between the first end 66 and the second end 68.

System 20 includes a first extender 34 and a second extender 36. First extender 34 includes an outer surface 38, which is configured for engagement with first collar 28. First extender 34 is configured for disposal with a concave portion of a spine. Second extender 36 includes an outer surface 40 configured for engagement with the second collar 30. Second extender 36 is configured for disposal with a convex portion of the spine. It is contemplated that system 20 may include one or a plurality of first extenders and/or second extenders.

System 20 includes a dorsal handle 46 disposed intermediate first end 24 and second end 26. Handle 46 is disposed perpendicular to axis L. Handle 46 includes a gripping surface for manipulation thereof. It is contemplated that handle 46 may be disposed in alternate orientations relative to axis L such as, for example, transverse and/or other angular orientations such as acute or obtuse, co-axial and/or may be offset or staggered.

System 20 includes a lateral handle 48 disposed adjacent second end 26. Handle 48 is disposed co-axial with axis L. It is contemplated that handle 48 may be disposed adjacent first end 28. Handle 48 includes a gripping surface for manipulation thereof. It is contemplated that handle 48 may be disposed in alternate orientations relative to axis L such as, for example, transverse, perpendicular and/or other angular orientations such as acute or obtuse and/or may be offset or staggered.

Handles 46, 48 are configured for manipulation and application of forces thereto to create one or a plurality of forces and/or moments for application to a body to create for example, a derotation force for a spinal treatment. In one embodiment, handle 46 and/or handle 48 can be removable for example, to reposition components of system 20 and/or modify treatment. It is envisioned that handles 46, 48 may be employed to displace, pull, twist or align vertebrae, according to the requirements of a particular application.

Figure 9:
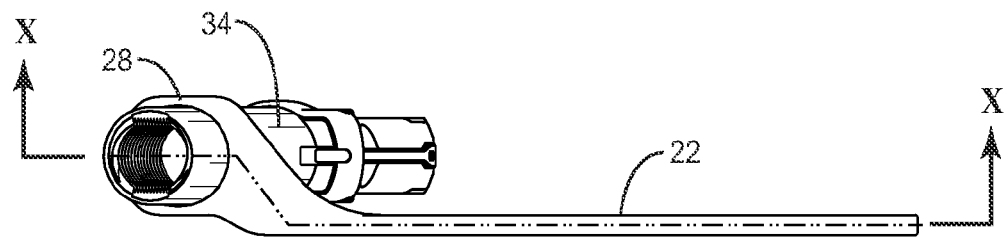
FIG. 9 is a top view of components of the system shown in FIG. 1.
Figure 10:
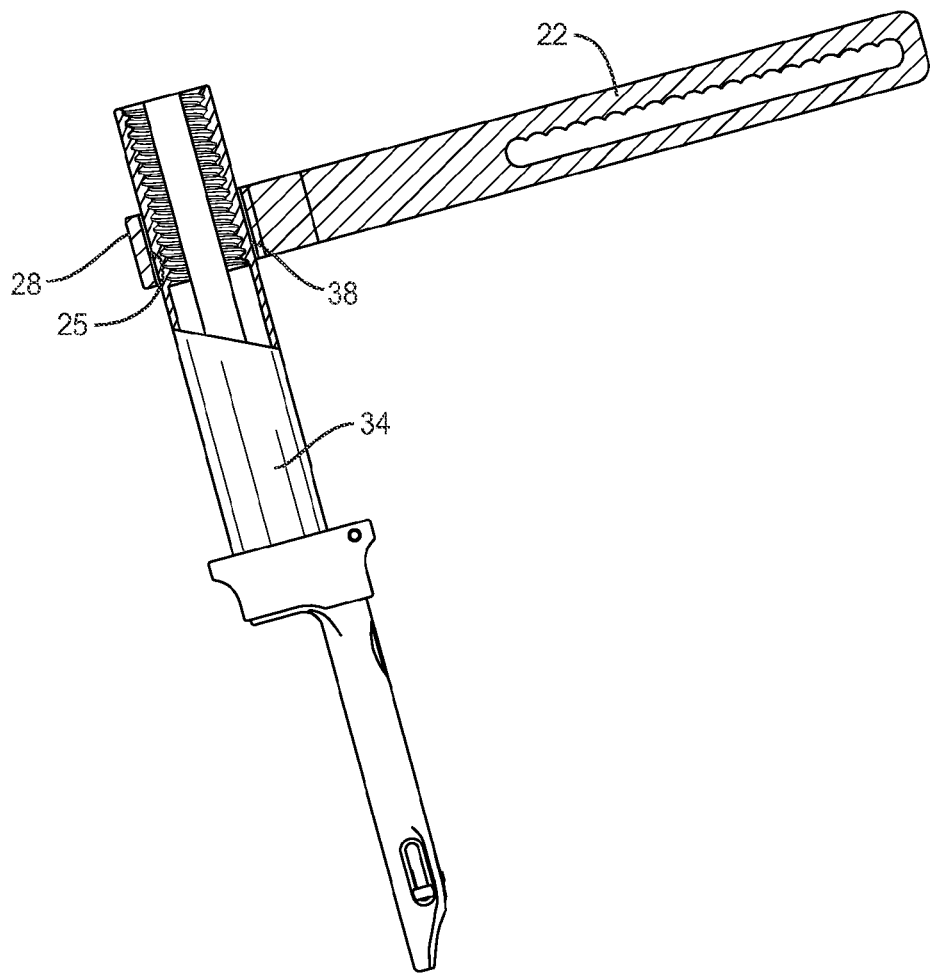
FIG. 10 is a side view, in part cross section, of the components of the system taken along the lines X-X shown in FIG. 9.
Figure 11:
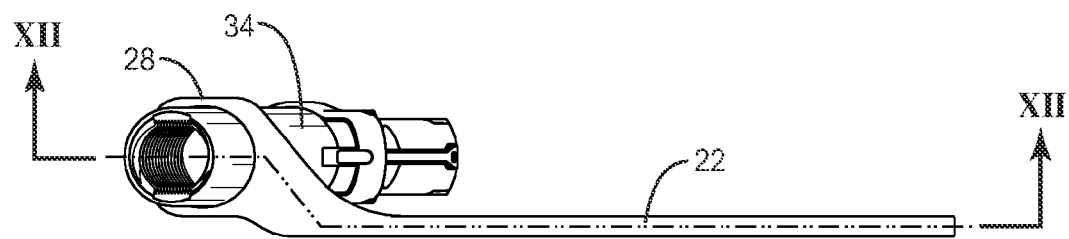
FIG. 11 is a top view of components of the system shown in FIG. 1.
Figure 12:
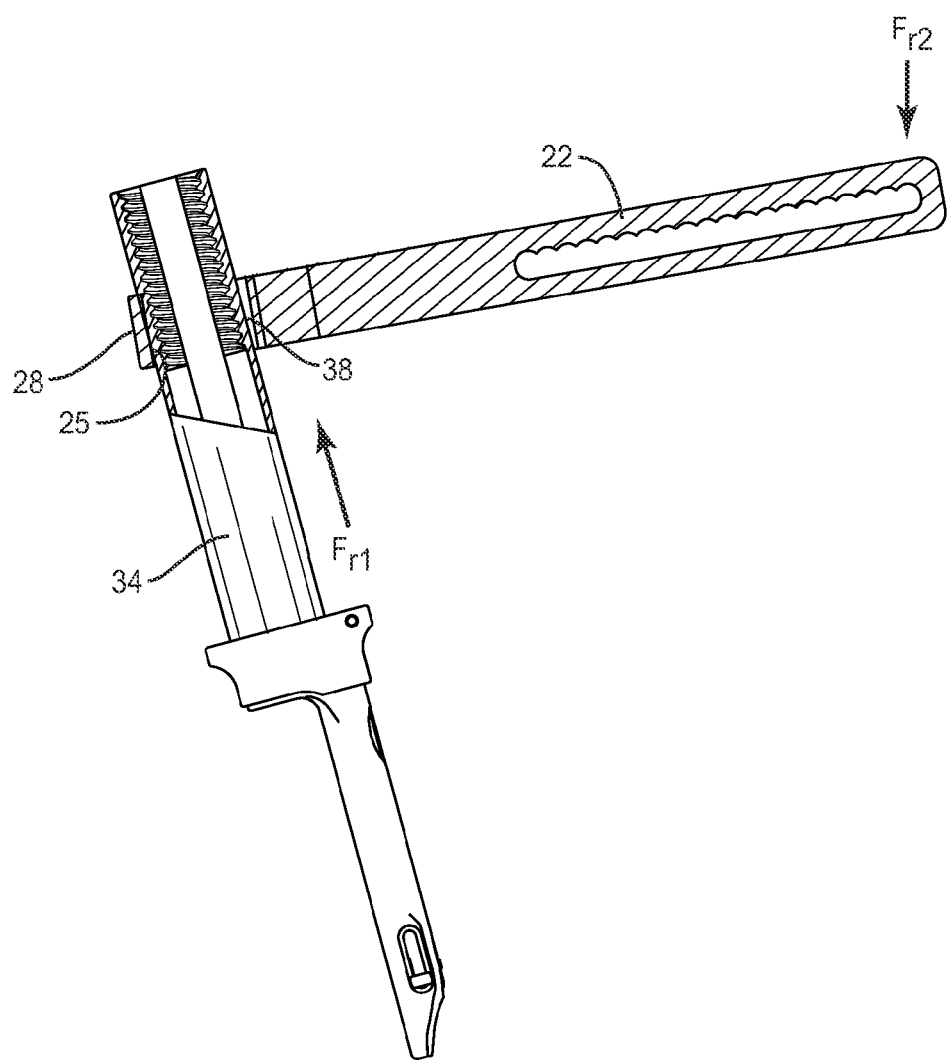
FIG. 12 is a side view, in part cross section, of the components of the system taken along the lines XII-XII shown in FIG. 11.

In operation, the components of system 20 are disposable between a first configuration (FIGS. 9 and 10) and a second configuration (FIGS. 11 and 12). In the first configuration, no appreciable force is applied to handles 46, 48. As such, no appreciable force is applied to bridge member 22. Outer surface 38 of extender 34 is freely slidable within inner surface of collar 28, as shown in FIG. 9. Post 62 is freely translatable with slot 32 and collar 30 is angularly movable relative to second end 26.

The components of system 20 are moved to the second configuration upon application of forces to handles 46, 48. A first force F1 is applied to handle 46, in the direction shown by the corresponding arrow in FIG. 8, and a second force F2 is applied to handle 48, in the direction shown by the corresponding arrow in FIG. 8. Application of forces F1, F2 create a moment M on bridge member 22. Application of moment M to bridge member 22 creates a resultant force Fr1 that drives inner surface 25 into fixed engagement with outer surface 38 and creates a resultant force Fr2 which, depending on the anatomy of a body and/or orientation of the components of system 20 including bone fasteners, forces post 62 into fixed engagement with a particular recess 43. In one embodiment, the fixed engagement of inner surface 25 with outer surface 38 results in a pivot coupling therebetween to fix collar 28 with extender 34.

In the second configuration, first collar 28 is locked with extender 34 and second collar 30 is locked to extender 36. The application of forces F1, F2 to handles 46, 48 can be maintained and/or increased to apply a treatment force, such as, for example, a derotation force to a body. It is envisioned that this configuration avoids the need for a separate locking structure to fix collars 28, 30 with extenders 34, 36. It is further envisioned that system 20 may be disposed in the second configuration by applying forces F1, F2 in alternate directions to that shown in FIG. 8, such as an opposite direction. In one embodiment, collar 28 can be locked into place along first extender 34 with a locking collar 54, as shown in FIG. 1.

In assembly, operation and use, spinal correction system 20, similar to the system described above, is employed with a surgical procedure, such as, for example, a correction treatment to treat adolescent idiopathic scoliosis and/or Scheuermann's kyphosis of a spine. It is contemplated that one or all of the components of spinal correction system 20 can be delivered or utilized as a pre-assembled device or can be assembled in situ.

For example, spinal correction system 20 can be employed with a surgical correction treatment of an applicable condition or injury of an affected section of a spinal column and adjacent areas within a body, such as, for example, vertebrae V, as shown in FIG. 1. It is envisioned that spinal correction system 20 may be employed with one or a plurality of vertebrae.

In use, to treat vertebrae V, a medical practitioner obtains access to a surgical site including vertebrae V in any appropriate manner, such as through incision and retraction of tissues. It is envisioned that spinal correction system 20 can be used in any existing surgical method or technique including open surgery, mini-open surgery, minimally invasive surgery and percutaneous surgical implantation, whereby vertebrae V is accessed through a mini-incision, or sleeve that provides a protected passageway to the area. Once access to the surgical site is obtained, the particular surgical procedure can be performed for treating the spine disorder.

An incision is made in the body of a patient and a cutting instrument (not shown) creates a surgical pathway for implantation of components of spinal correction system 20. A preparation instrument (not shown) can be employed to prepare tissue surfaces of vertebrae V, as well as for aspiration and irrigation of a surgical region according to the requirements of a particular surgical application.

Pilot holes (not shown) are made bilaterally in selected levels of vertebrae V for receiving bone fasteners 70, 72. Extenders 34, 36 are oriented for manipulation, alignment and capture of bone fasteners 70, 72. First extender 34 is configured for disposal with a concave portion of a selected vertebra of vertebrae V and second extender 36 is configured for disposal with a convex portion of a selected vertebra of vertebrae V.

Extenders 34, 36 are attached with vertebrae V via bone fasteners 70, 72, such that the components of system 20 are disposed in the first configuration, as described above and shown in FIGS. 9 and 10. Force F1 is applied to handle 46, in the direction shown by the corresponding arrow in FIG. 8, and force F2 is applied to handle 48, in the direction shown by the corresponding arrow in FIG. 8, to create moment M on bridge member 22. Moment M creates force Fr1 that drives inner surface 25 into fixed engagement with outer surface 38 and creates force Fr2 to force post 62 into fixed engagement with a recess 43, as shown in FIG. 1.

First collar 28 is locked with extender 34 and second collar 30 is locked to extender 36 such that spinal correction system 20 is disposed in the second configuration. The application of forces F1, F2 to handles 46, 48 can be maintained and/or increased to apply a derotation force to vertebrae V.

It is envisioned that the use of microsurgical and image guided technologies may be employed to access, view and repair spinal deterioration or damage, with the aid of spinal correction system 20. Upon completion of the procedure, the surgical instruments and assemblies are removed and the incision is closed.

It is contemplated that the components of spinal correction system 20 may be employed to treat progressive idiopathic scoliosis with or without sagittal deformity in either infantile or juvenile patients, including but not limited to prepubescent children, adolescents from 10-12 years old with continued growth potential, and/or older children whose growth spurt is late or who otherwise retain growth potential. It is further contemplated that the components of spinal correction system 20 and method of use may be used to prevent or minimize curve progression in individuals of various ages.

Figure 13:
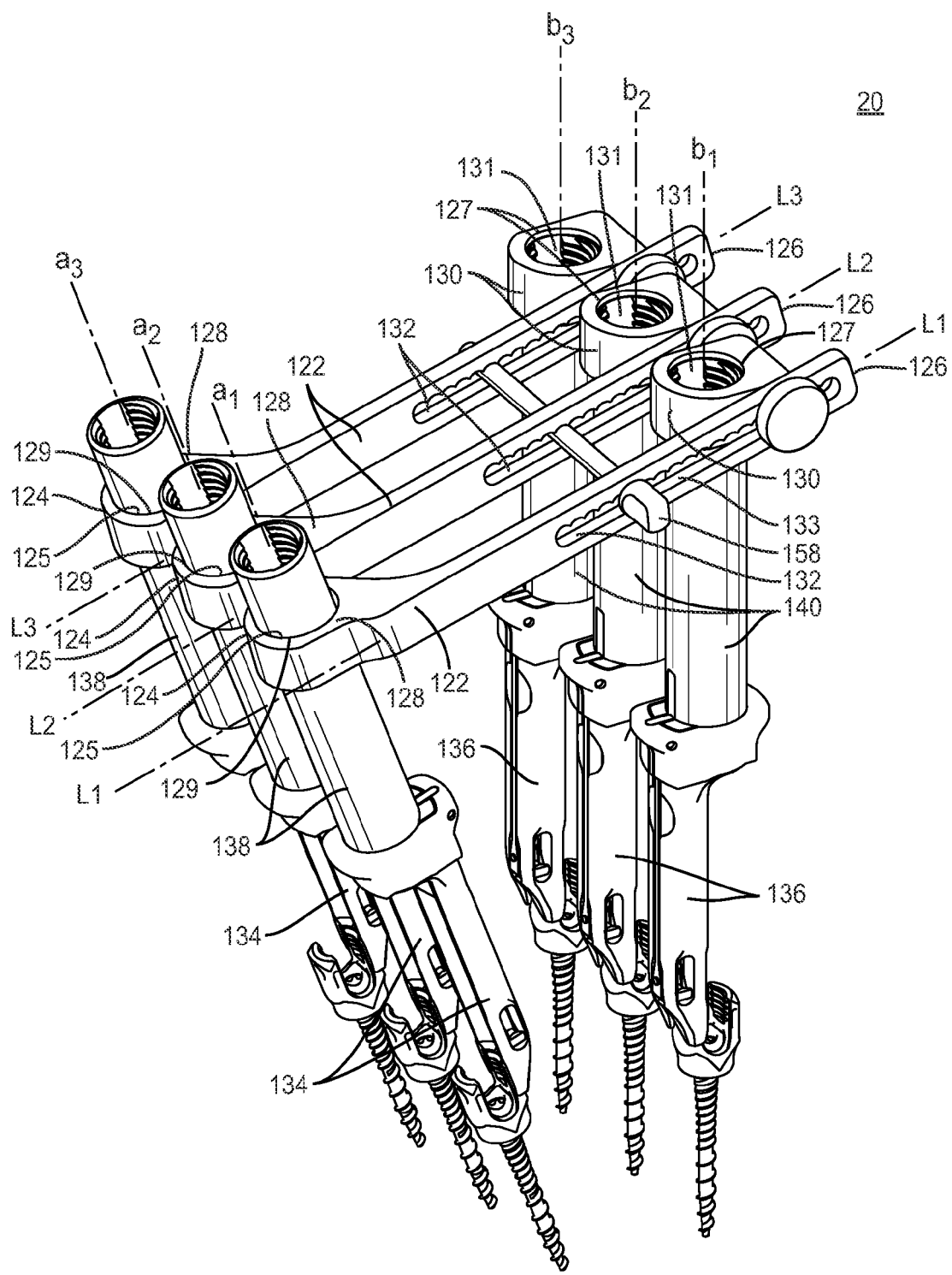
FIG. 13 is a perspective view of one embodiment of the system shown in FIG. 1.
Figure 14:
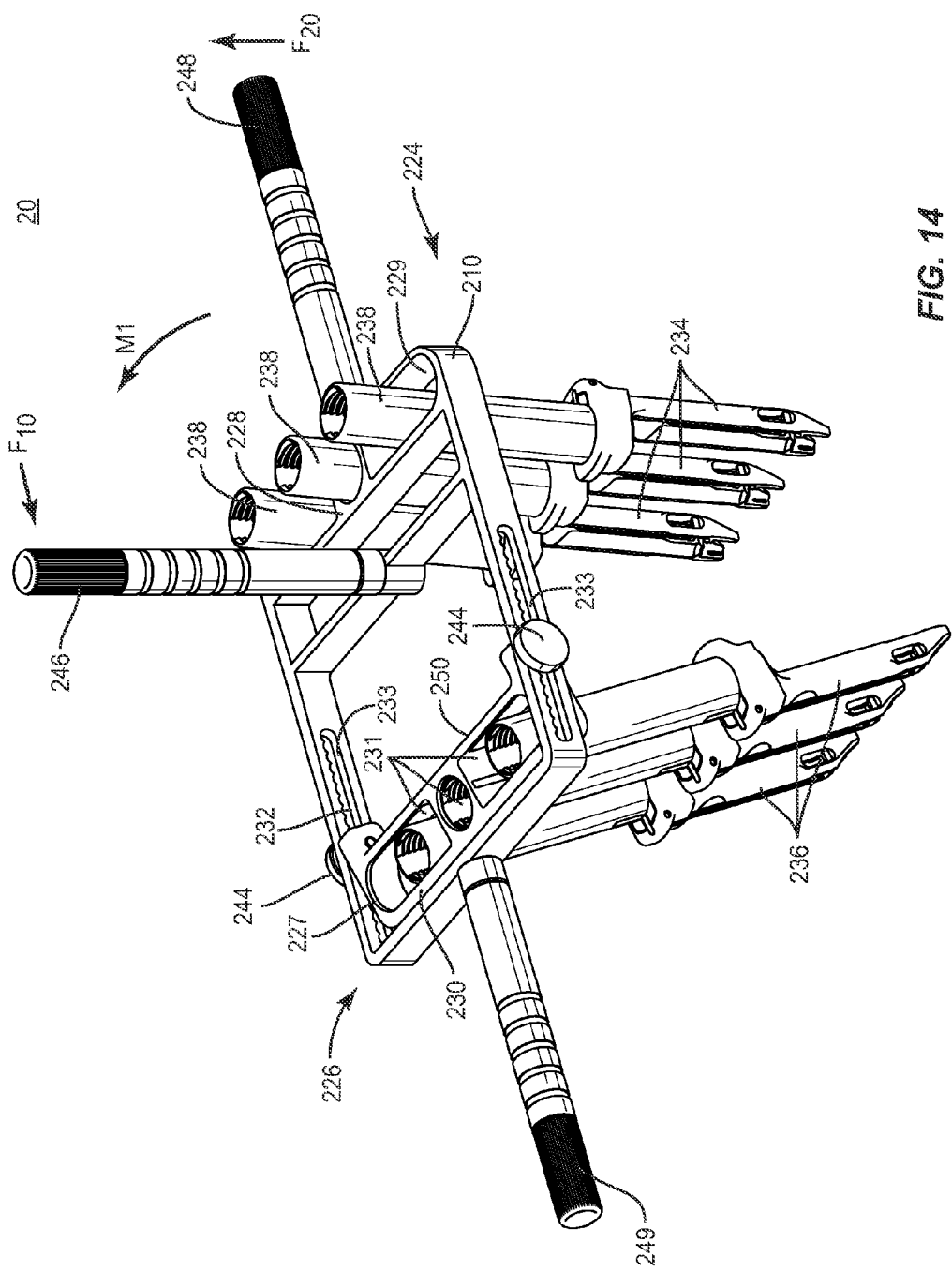
FIG. 14 is a perspective view of one embodiment of the system shown in FIG. 1.
Figure 17:
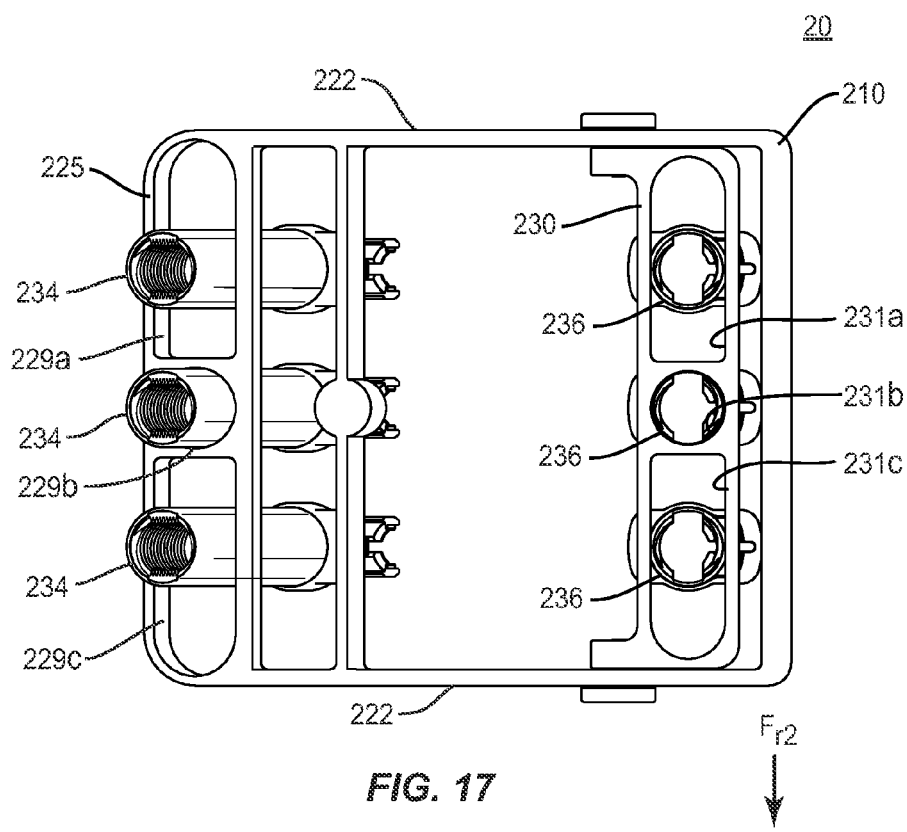
FIG. 17 is a top view of the system shown in FIG. 14.
Figure 18:
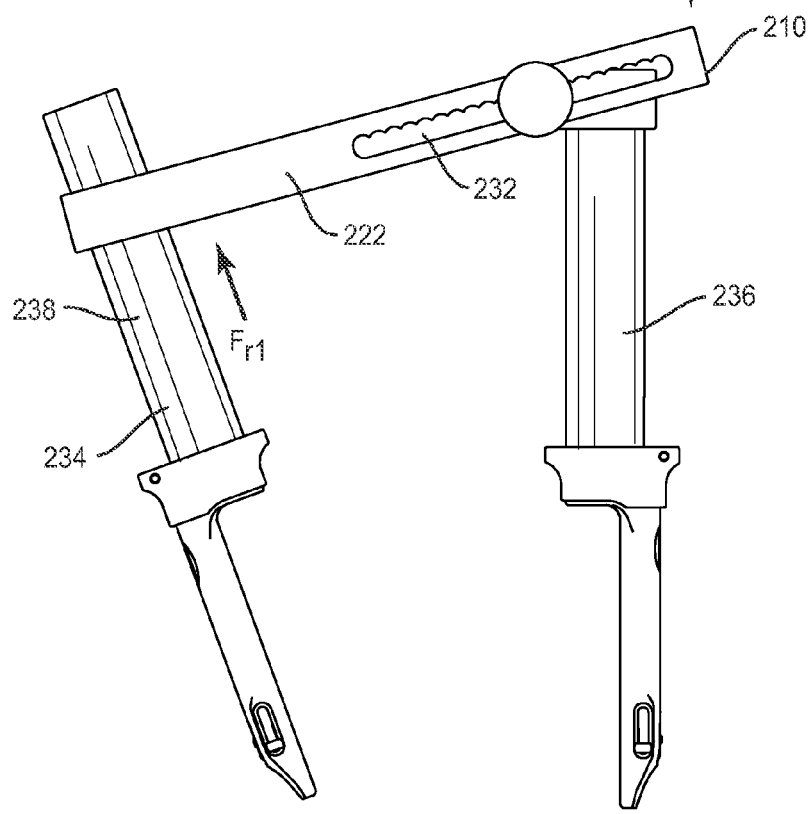
FIG. 18 is a side view of the system shown in FIG. 14.

In one embodiment, as shown in FIG. 13, a spinal correction system 20, similar to system 20 described above with regard to FIGS. 1-12, includes a plurality of bridge members 122. The plurality of bridge members 122 define longitudinal axes L1, L2 and L3, respectively. Each bridge member 122 extends between a first end 124 and a second end 126. First end 124 includes a first collar 128 having an inner surface 125. Inner surface 125 defines a first opening 129. Second end 126 includes a second collar 130 having an inner surface 127. Inner surface 127 defines a second opening 131. First openings 129 define first axes a1, a2 and a3, respectively, oriented transverse and movable relative to the respective axes L1, L2 or L3. Second openings 131 define second axes b1, b2 and b3, respectively, oriented transverse to the respective axes L1, L2 or L3.

Second end 126 includes an interior surface 133 defining an elongated slot 132 configured for selectively moving second collar 130 relative to bridge member 122 in at least one orientation, similar to that described above, relative to axes L1, L2 or L3. A plurality of first extenders 134, each having an outer surface 138, which is configured for engagement with first collar 128. A plurality of second extenders 136, each having an outer surface 140 configured for engagement with second collar 130.

The plurality of bridge members 122 is disposed in a linked configuration. Elongated slots 132 are configured for disposal of a link member 158 for linking the elongated members. Linking the plurality of bridge members 122 allows for global derotation of multiple vertebrae. Each of the bridge members 22 is disposable between a first configuration and a second configuration, as described above with regard to FIGS. 1-12. It is contemplated that each of the plurality of bridge members 22 may include handles, such as handles 46, 48 described above, to apply forces to system 20, or may include one set of handles 46, 48 for all bridge members 22.

In one embodiment, as shown in FIGS. 14-18, a spinal correction system 20, similar to system 20 described above with regard to FIGS. 1-12, includes a bridge member, such as, for example, a frame 210. Frame 210 extends between a first end 224 and a second end 226.

First end 224 includes a first collar 228 having an inner surface 225. Inner surface 225 defines a plurality of cavities including openings 229a, 229b, 229c. Opening 229a has an elongated configuration, opening 229b has a circular configuration and opening 229c has an elongated configuration. Openings 229a, 229b, 229c are each configured for disposal of a surgical instrument, such as, for example, extenders 234. It is contemplated that openings 229a, 229b, 229c may have other configurations, such as, for example, a singular elongated opening.

Second end 226 includes a second collar 230 having a second inner surface 227. Inner surface 227 defines a plurality of cavities including openings 231a, 231b, 231c. Opening 231a has an elongated configuration, opening 231b has a circular configuration and opening 231c has an elongated configuration. Openings 231a, 231b, 231c are each configured for disposal of a surgical instrument, such as, for example, extenders 236. It is contemplated that openings 231a, 231b, 231c may have other configurations, such as, for example, a singular elongated opening.

Collar 230 includes a pair of opposing hinges 244 disposed on lateral sides of frame 210. Collar 230 includes threaded openings 260 that receive hinges 244. Each hinge 244 includes a post 262 configured for engagement with opening 260. Hinge 244 is configured for movable disposal relative to second end 226. Second collar 230 includes a shoulder 250 configured for preventing translation of second extender 236 out of second collar 236.

Second end 226 includes an interior surface 233 that defines an elongated slot 232 configured for movement of second collar 230 including hinge 244 relative to frame 210 in at least one orientation, as described above. Interior surface 233 of slot 232 incuides projections 242 that define recesses 243 configured for disposal of post 262. Hinge 244 moves along the length of slot 232.

System 20 includes a dorsal handle 246, a first side handle 248 and a second side handle 249, similar to the handles described above. Handles 246, 248, 249 are configured for manipulation and application of forces thereto to create one or a plurality of forces and/or moments for application to a body to create for example, a derotation force for a spinal treatment. In operation, the components of system 20 are disposable between a first configuration and a second configuration. In the first configuration, no appreciable force is applied to frame 210, similar to that described above.

In one embodiment, the components of system 20 are moved to the second configuration upon application of forces to handles 246, 248. A first force F10 is applied to handle 246, in the direction shown by the corresponding arrow in FIG. 14, and a second force F20 is applied to handle 248, in the direction shown by the corresponding arrow in FIG. 14. Application of forces F10, F20 create a moment M1 on frame 210. Application of moment M1 to frame 210 creates a resultant force Fr10 that drives inner surface 225 into fixed engagement with outer surfaces 238 and creates a resultant force Fr20 which, depending on the anatomy of a body and/or orientation of the components of system 20 including bone fasteners, forces opposing posts 262 into fixed engagement with particular opposing recesses 243. In the second configuration, collar 228 is locked with extenders 234 and second collar 230 is locked to extenders 236. The application of forces F10, F20 to handles 246, 248 can be maintained and/or increased to apply a treatment force, such as, for example, a derotation force to a body.

In one embodiment, the components of system 20 are moved to the second configuration upon application of forces to handles 246, 249, such that a force F10 is applied to handle 246, and a force is applied to handle 249 in a downward direction.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A spinal correction system comprising:
    at least one elongate member defining a longitudinal axis and extending between a first end and a second end, the first end including a first inner surface defining a first cavity that is fixed relative to the elongate member and the second end including a collar having a second inner surface defining a second cavity, the second cavity being movable relative to the elongate member in at least one orientation, the second end comprising an interior surface defining an elongated cavity;
    at least one first extender defining a first outer surface that engages the first inner surface; and
    at least one second extender defining a second outer surface configured for engagement with the second inner surface,
    wherein the at least one elongate member is disposable between a first configuration and a second configuration such that the second cavity is selectively movable in the at least one orientation to a position such that the first inner surface is forcibly disposable in a fixed engagement with the first outer surface and the interior surface is forcibly disposed in a second fixed engagement with at least a portion of the collar;
    wherein the first and second inner surfaces include a plurality of projections defining a plurality of recesses therebetween, such that in the second configuration, the collar is disposed in one of the plurality of recesses.

2. The system as recited in claim 1, wherein the fixed engagement includes a pivot coupling between the first inner surface and the first outer surface.

3. The system as recited in claim 1, wherein the elongated cavity includes a slot and the collar includes a post configured for fixation with the interior surface.

4. The system as recited in claim 1, wherein the collar includes a hinge having a post configured to fix the collar with the elongated member in the position.

5. The system as recited in claim 1, wherein the interior surface includes a scalloped configuration.

6. The system as recited in claim 1, wherein the second cavity defines a second axis oriented transverse and is movable relative to the longitudinal axis.

7. The system as recited in claim 1, wherein the at least one orientation includes an angular orientation and an axial orientation relative to the longitudinal axis.

8. The system as recited in claim 1, further comprising at least one handle attached with the at least one elongate member.

9. The system as recited in claim 1, wherein the first end includes a collar defining an opening extending therethrough and the collar of the second end includes a flange configured for engaging the second extender.

10. The system as recited in claim 1, wherein the collar includes a shoulder configured for preventing ventral translation of the second extender.

11. The system as recited in claim 1, wherein the first extender comprises a locking collar configured for engaging the first end of the at least one elongate member.

12. The system as recited in claim 1, wherein the first extender is configured for disposal with a concave portion of a spine and the second extender is configured for disposal with a convex portion of the spine.

13. The system as recited in claim 1, wherein the system is configured for derotation of vertebrae such that a first force oriented in a first direction is applied to the first end and a second force oriented in a second direction is applied to the second end.

14. The system as recited in claim 1, wherein the at least one elongate member includes a plurality of elongated members disposed in a linked configuration.

15. The system as recited in claim 14, wherein each of the elongate cavities of the second end are configured for disposal of a link member for linking the elongated members.

16. The system as recited in claim 1, wherein the at least one elongated member includes a frame and the first inner surface defines a plurality of first cavities configured for disposal of a plurality of first extenders and the second inner surface defines a plurality of second cavities configured for disposal of a plurality of second extenders.

17. The system as recited in claim 16, wherein the plurality of first cavities and the plurality of second cavities are aligned in a transverse orientation relative to the longitudinal axis.

* * * * *